United States Patent [19]
Lenhart et al.

[11] 3,978,491
[45] Aug. 31, 1976

[54] METHOD AND SYSTEM FOR RECORDING HEART LEAD TRACINGS ON SEGMENTS OF AN EKG DATA STRIP AND FOR DETACHING AND TRANSFERRING THE SEGMENTS TO A PERMANENT FILE

[76] Inventors: Gerry Anne Lenhart; Lawrence Donald Lenhart, both of 1235 W. 31st Ave., San Mateo, Calif. 94403

[22] Filed: Jan. 10, 1975

[21] Appl. No.: 540,005

[52] U.S. Cl. ............................. 346/1; 346/33 ME; 346/134; 206/390; 206/820; 128/2.06 G
[51] Int. Cl.² .................... G01D 9/12; G01D 15/34
[58] Field of Search ................. 346/1, 33 ME, 134; 206/390, 820; 128/2.06 R, 2.06 G

[56] References Cited
UNITED STATES PATENTS

| | | | |
|---|---|---|---|
| 2,346,219 | 4/1944 | Johnson | 206/390 X |
| 3,085,024 | 4/1963 | Blackfod | 206/820 X |
| 3,143,208 | 8/1964 | Sizemore, Jr. | 206/820 X |
| 3,287,814 | 11/1966 | Littmann | 128/2.06 R X |
| 3,302,639 | 2/1967 | Koffler | 346/134 X |
| 3,333,688 | 8/1967 | Green, Jr. | 206/390 X |

FOREIGN PATENTS OR APPLICATIONS

| | | | |
|---|---|---|---|
| 975,104 | 11/1964 | United Kingdom | 346/134 |

*Primary Examiner*—Stanley J. Witkowski
*Attorney, Agent, or Firm*—Owen, Wickersham & Erickson

[57] ABSTRACT

An electrocardiogram (EKG) data strip is constructed with contiguous, repetitive segments to allow individual heart lead tracings recorded on the segments to be readily removed from the EKG data strip after the tracings have been completed so that the segments can then be inserted directly into a permanent record form.

The EKG data strip of the present invention has a first longitudinal line of perforations along one edge, a second longitudinal line of perforations adjacent the other edge and a plurality of transverse lines of perforations extending across the EKG data strip between the first and second longitudinal lines of perforations. The transverse lines of perforations are located at spaced intervals along the length of the EKG strip to thereby divide the central part of the strip into a plurality of longitudinally aligned segments, each of which has a predetermined width between the longitudinal perforations and a predetermined length between two adjacent transverse perforations.

Each segment is readily detachable from the EKG data strip along the longitudinal and transverse perforations. The segments can be detached as individual, single segments, or two or more contiguous segments can be detached to provide a rhythm strip in which adjacent segments are connected together by undetached transverse perforation lines between the adjacent segments.

17 Claims, 12 Drawing Figures

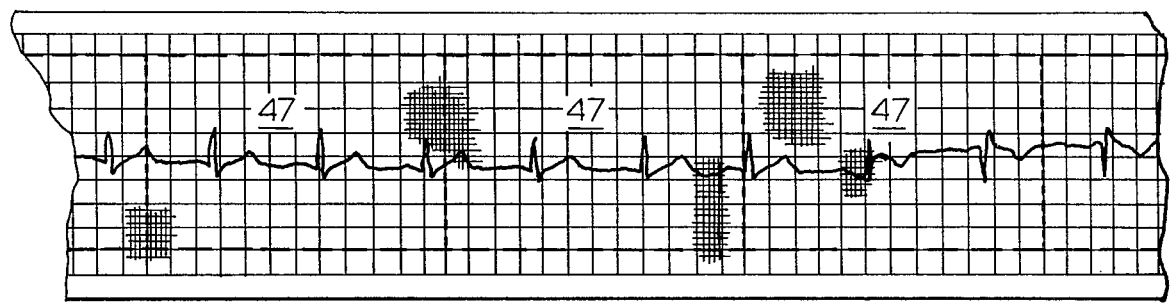
FIG. 3-A
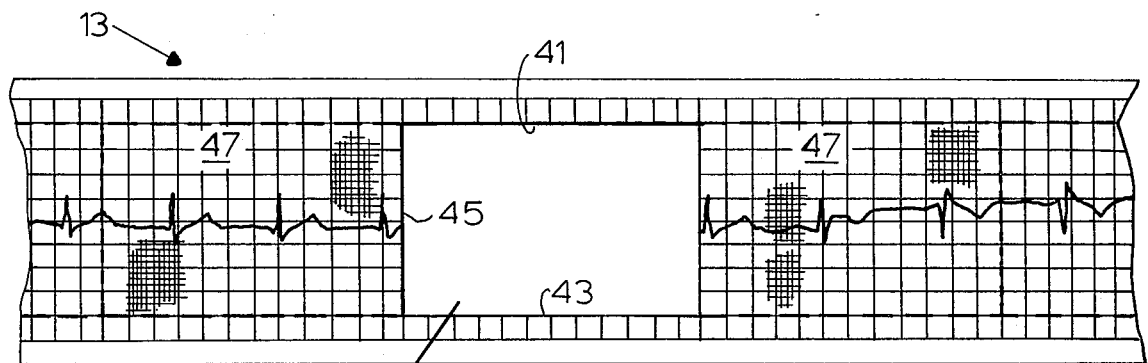
FIG. 3-B
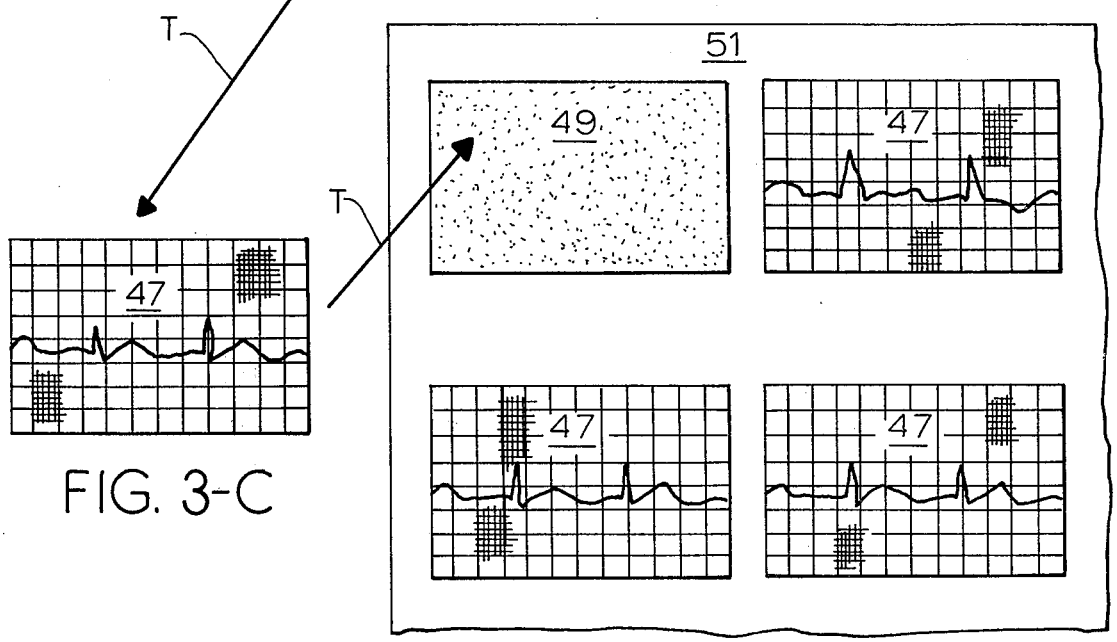
FIG. 3-C
FIG. 3-D

FIG. 4
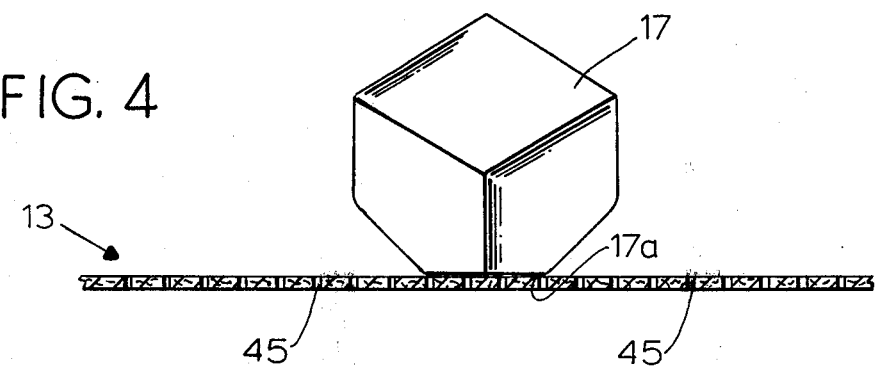
FIG. 5
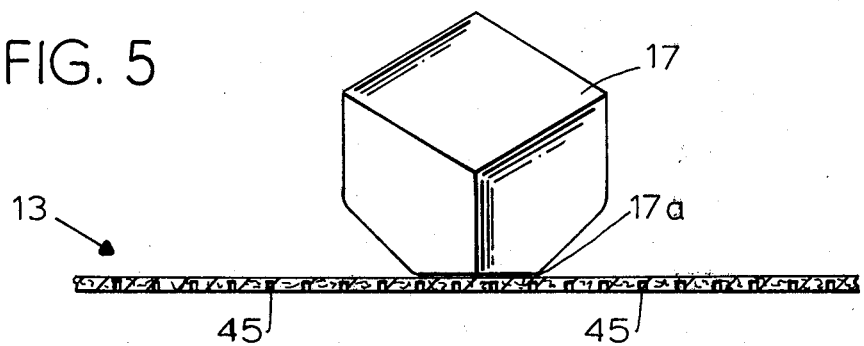
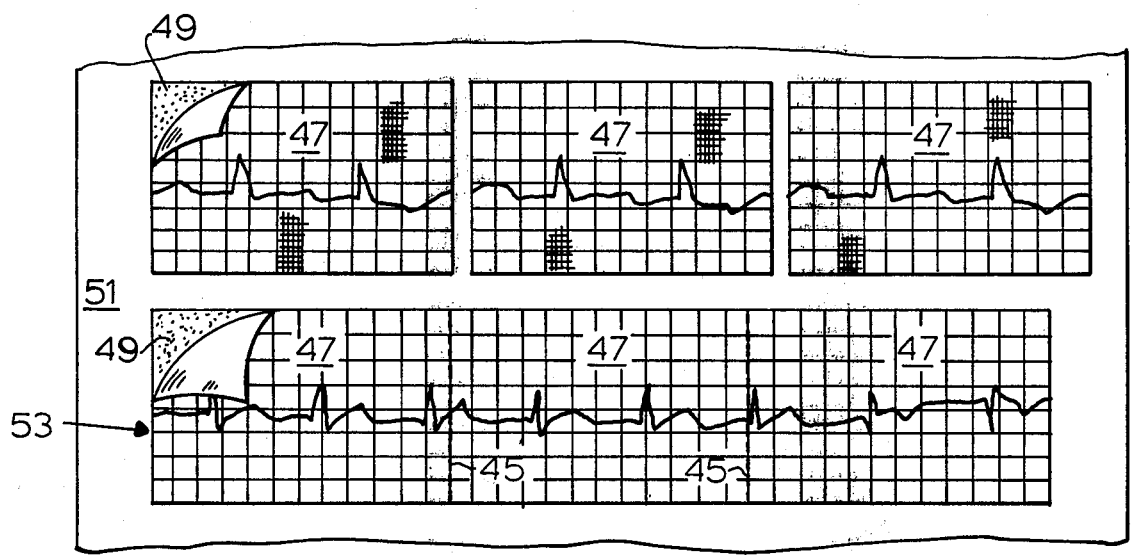
FIG. 6

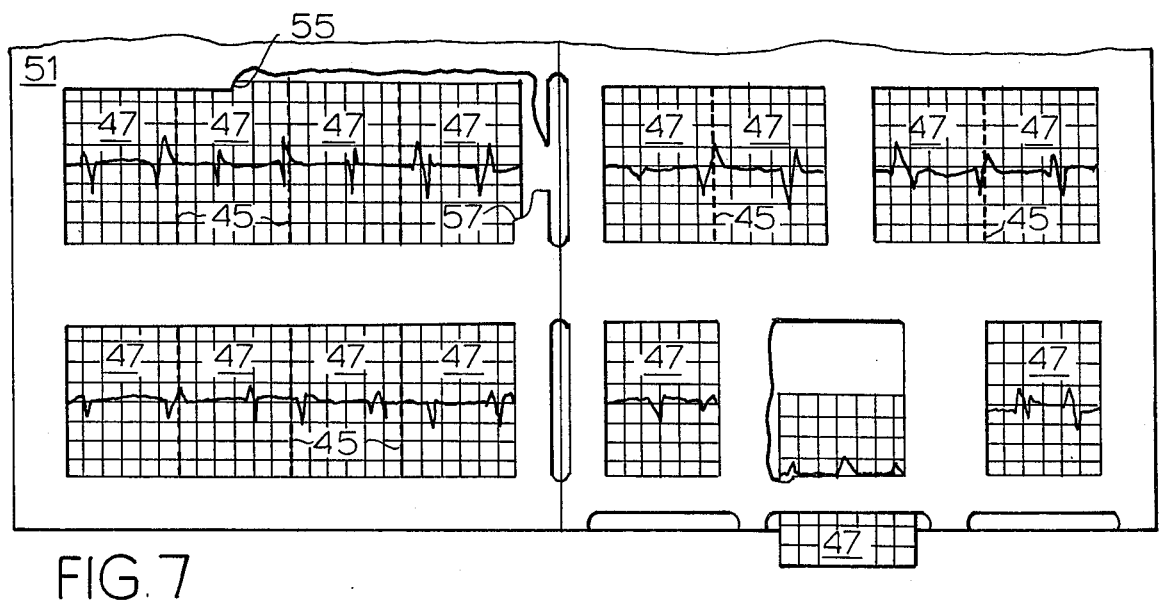
FIG. 7
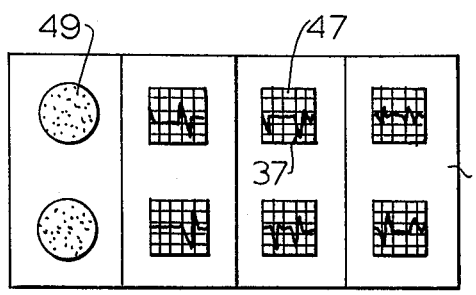
FIG. 8
FIG. 9
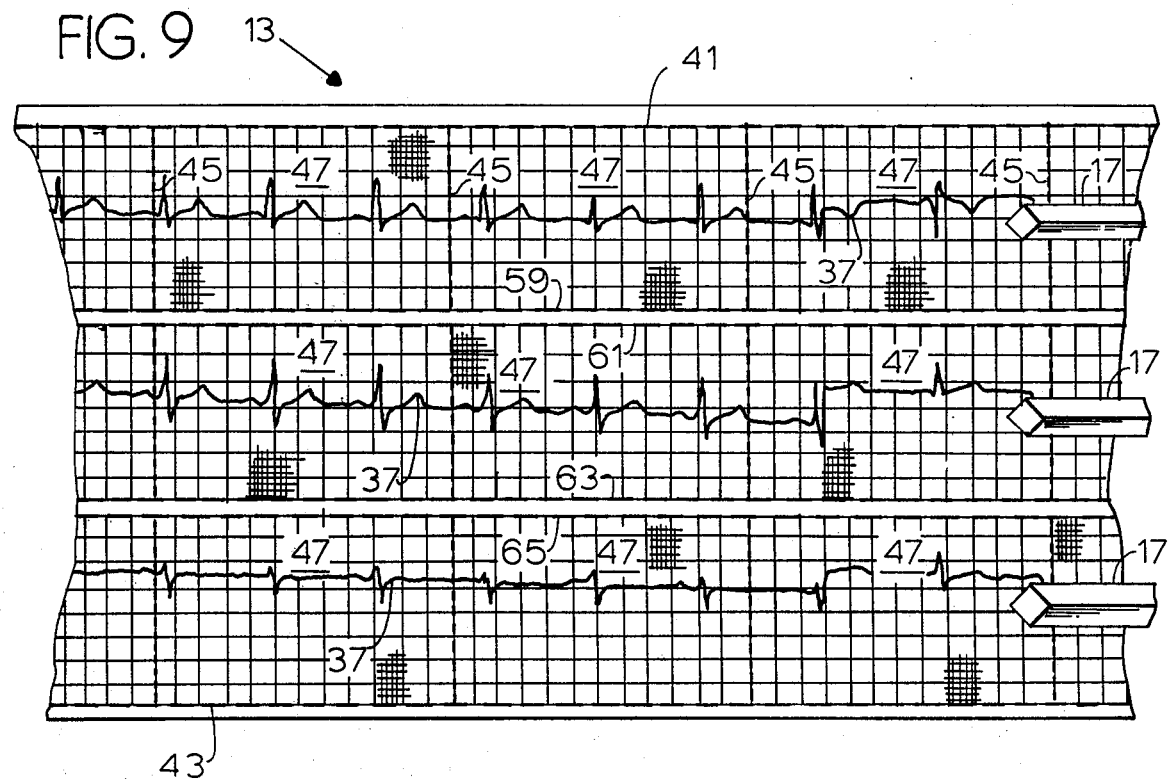

METHOD AND SYSTEM FOR RECORDING HEART LEAD TRACINGS ON SEGMENTS OF AN EKG DATA STRIP AND FOR DETACHING AND TRANSFERRING THE SEGMENTS TO A PERMANENT FILE

BACKGROUND OF THE INVENTION

This invention relates to a method and a system of preparing an electrocardiogram (EKG) data strip for individual heart lead tracings to be transferred into a permanent record file. The present invention relates particularly to a system in which the tracings can be easily and simply removed from the strip after the tracing has been completed. The detached tracing can then be inserted directly into the record form.

The present invention is a labor saving construction of a widely used medical product, and it provides a considerable saving of time and money by physicians and their technicians, EKG paper is made up in strip form, wound into a roll and used inside an electrocardiogram machine. The machine unrolls the EKG paper as a stylus permanently marks the heart tracing on the paper. The paper itself is a highly specialized paper which has a line grid on one surface, and the paper is, in a majority of cases, heat sensitive so that the stylus actually burns the tracing onto this grid surface of the strip as the strip is pulled through the machine and beneath the stylus at a fixed paper speed of 25mm per second. This speed is determined by the pull of a special roller some distance from the stylus. The timing, speed, meterage, and quality of the EKG paper are all carefully calibrated to insure maximum accuracy. Portions of the tracings recorded on the strip are cut from the strip after recording, and stored in a permanent record holder.

There is a decided need in the field of cardiology for an efficient method of transferring essential, measured parts of the long specialized data strip into the permanent record holder (often a large mounting pad). For example, on taking one individual's EKG, there are 12 separate and distinct wave patterns (labeled leads I, II, III, aVR, aVL, aVF, $V_1-V_6$) which are traced on the elongated strip. For subsequent measurement of the various wave lengths and amplitudes it has been found convenient to first transfer typical segments of these wave forms onto a permanent record holder and then to give a complete interpretation in writing on another part of that record holder.

At this point a time consuming task is involved in transferring the 12 leads onto the separate record holder. These 12 separate leads must be cut individually into predetermined pieces so as to fit the record sheet. This cutting currently is being performed by a number of machines -- some simple and others more expensive and complex, but all of which are still rather laborious. In addition to be costly, these machines are all still time consuming since these devices involve a cutting process which is carried out by hand, either with s stamper or by the use of hand tools. Neither cutting process is satisfactory for the physician in private practice or large medical centers, where hundreds of EKG's must be mounted in any given day.

The prior art systems required first marking the tape to locate the individual recordings from the 12 different EKG leads, then cutting out the market individual recordings (either by hand tools or by some cutting device) and finally mounting the separated recordings in the record holder.

Numerous attempts have been made to mechanize this operation, but none of the techniques used prior to the present invention have proved satisfactory.

One example of a mechanical cutting device which has been developed for this purpose is shown in U.S. Pat. No. 3,261,250 to Parks et al. The Parks device is a typical example of a hand stamper.

A major drawback to the Parks device is the fact that it has a single cutting plate which limits its use to single length portions for only one specific mounting card. This is a problem because the typical mounted EKG record card usually contains several ryhthm strips which are longer than the single length portions in order to determine and illustrate the individual's heart rhythm.

Depending on the calibration of the electrocardiogram machine and the brand of data strip used, the cutting device for the Parks et al patent can also present problems in chopping off the upper and lower peaks of tracings. This is a special problem because it is something that is not discovered until recording has been completed, and the strip has been cut.

The Parks device also presents the usual problems of replacing blades when the cutting blades become dull.

Another example of a mechanical cutting device is shown in U.S. Pat. No. 3,817,137 to Thatcher. This device uses a more or less standard paper cutter type of blade in combination with a rather complex viewing and cutting system for the data strip. The Thatcher device requires the data strip to be fed through a track system in the machine. As it is fed through the track, it is scanned and cut with successive up and down manual movements of the cutting blade. All in all it is a rather awkward, laborious system.

A third example of apparatus which has been developed to assist in mounting the tracings in U.S. Pat. No. 3,382,127 to Littmann et al. The Littmann et al device comprises a frame which acts as a press to mount tracings (previously cut from an EKG recording strip) onto an adhesively coated record card.

A further drawback to the prior art existing prior to the present invention was the fact that these devices could accommodate only a standard width EKG paper designated to record a single channel. Several new EKG machines have been introduced which are able to record two and three wave patterns simultaneously, using multiple systems and a considerably wider strip of paper. These newer EKG machines and wider strips of paper entail additional hand cutting steps just to utilize these prior art devices, which is, of course, no solution to the existing handling problem in this art.

There is a definite need to avoid the use of such cutting devices which are burdensome, limited in scope, costly and which quickly become obsolete.

There is also a need for a system which provides easy detachment of portions of varying lengths, which is economical to use, and which is easily adapted to differing and newly developing systems.

It is a primary object of the present invention to perforate specialized EKG paper for the purpose of selecting desired portions, in either single or multiple lengths, in order to facilitate both the detachment of these portions and the transfer onto a permanent record holder.

It is another important object of the present invention to perforate the specialized EKG paper in a particular way so as to allow an efficient transfer of particular portions onto a permanent record holder. The mounting cards in current use have fixed spaces with certain dimensions set aside for attaching EKG strip segments. The present invention permits these dimensions to be perforated into the EKG strip initially so as to eliminate the need for hand cutting later by scissors or other devices.

Another specific object of the present invention is to perforate the EKG paper into predetermined, contiguous, repetitive segments. This allows easy separation of single segments or multiple segments. This also allows physicians or technicians to mark the important segments easily, thereby allowing less skilled personnel to perform the simple task of detaching the segments and transferring them onto the permanent record.

A further object of the present invention is to facilitate performing the EKG tracing itself. The manner in which the EKG data strip is perforated allows the cardiology technician to be able to see at a glance whether the tracing complexes will fit into the segment dimensions. This avoids wrong guesses. It further allows the technician to make adjustments, if necessary, in the course of performing the tracing (e.g., an increase or a decrease in sensitivity), to thereby eliminate unnecessary repeat tracings. It also avoids the problem of chopping off part of the top or bottom of a tracing by a mechanical cutter after the tracing has been completed, and often after the leads have been disconnected from the patient.

There is a tendency, especially prevalent with technicians that are fairly new, to take excessively long tracings. With the present invention most of the recordings are kept quite short because the length of the recording needed can be seen at a glance. That is, a technician can actually see the perforations bounding the segment, and he can discontinue the tracing at the end of the desired segment. This results in a saving of costly paper and can result in substantial savings.

Another object of the present invention is to allow adaptation to any mounting system in use. This adaptation is accomplished while still permitting the EKG data strip to be used in all existing EKG machines with no modification of the machine required. This feature of the present invention thus provides the simplest, most economical approach to the problem of accommodating a wide variety of mounting record cards.

A further object of the present invention is to allow easy adaptation to new and developing systems intended for multiple, simultaneous recordings. The perforated EKG data strip of the present invention can, for example, readily be adapted for use with machines which ran three leads at one time.

SUMMARY OF THE INVENTION

The present invention provides a method and a system of preparing an EKG data strip for individual heart lead tracings to be detached and transferred into a permanent record file.

In the present invention the specialized EKG data strip has a first longitudinal line of perforations formed adjacent one side edge and a second longitudinal line of perforations formed adjacent the other side edge. A plurality of transverse lines of perforations extend across the EKG data strip between the first and second longitudinal lines of perforations and at spaced intervals along the length of the EKG strip to thereby divide the central part of the strip into a plurality of longitudinally aligned segments, each of which has a predetermined width between the longitudinal perforations and a predetermined length between two adjacent transverse perforations. Each of the segments is readily detached from the EKG data strip along the longitudinal and transverse perforations.

The heart tracing is recorded on the EKG data strip between the longitudinal perforation lines, and the recording is detached from the rest of the strip by tearing along the longitudinal and transverse lines bounding the recording. The detached part may comprise a single segment, or it may comprise a rhythm strip made up of two or more immediately adjacent segments.

In making the recording, the amplitude of the electrocardiograph machine is regulated to insure that the maximum amplitude of the heart trace signal, during the recording of the heart tracing, falls within the existing width between the two longitudinal perforations. This insures that the full amplitude of the tracing will be recorded within the width of the detachable segment.

After the segments bearing the recording have been detached from the rest of the strip, the recording is transferred to and mounted in a permanent record file. The recording may be pressed in place on cards having precoated adhesive mounts, or it may be slipped into a frame retainer on cards having this type of mount.

The perforations are preferably formed on the back side of the strip, that is, the side opposite that bearing the line grid presented to the stylus. In this form of the invention the slits preferably do not extend completely through the thickness of the paper so that the upper, recording surface presents no obstruction to the movement of the stylus across the width of the data strip in the course of making a tracing.

In a second embodiment of the present invention, the perforations do extend completely through the width of the paper. In this construction each slit of the transverse perforations preferably has a length substantially less than that of the width of the stylus so that the stylus easily bridges two or more perforations. This minimizes any tendency of the perforations to interfere with the movement of the stylus across the width of the data strip during the recording.

In another emodiment of the present invention, an EKG data strip designed for recording multiple tracings side by side has additional longitudinally extending perforations extending parallel to the perforations of the first and second lines. These additional longitudinal perforations divide the width of the strip into two or more longitudinal strips, each of which is adapted to record a tracing from an associated stylus. The perforation pattern with these multiple stylus recording strips permit any number of individual segments, of any desired length and width, to be readily recorded, then detached from the master strip and subsequently transferred into permanent record files without requiring any auxiliary, complicated, costly, or hard to use mechanical devices.

Other and further objects of the present invention will be apparent from the following description and claims and are illustrated in the accompanying drawings which, by way of illustration, show preferred embodiments of the present invention and the principles thereof and what are now considered to be the best modes contemplated for applying these principles. Other embodiments of the invention embodying the same or equivalent principles may be used and struc-

BRIEF DESCRIPTION OF THE DRAWINGS

FIG. 1 shows the machine in the process of making heart lead tracings on an EKG data strip constructed in accordance with one embodiment of the present invention;

FIGS. 3A through 3D are sequence views showing:

In FIG. 3A, the EKG data strip with a recording as in FIG. 2;

In FIG. 3B, the data strip with one perforated segment detached;

In FIG. 3C, the perforated segment which has been detached from the strip in FIG. 3B; and In FIG. 3D, how the detached segment is transferred to and mounted on a permanent record form;

FIG. 4 is a fragmentary end elevation view, taken along the line and the direction indicated by the arrows 4—4 in FIG. 2, showing perforations which extend completely through the thickness of the EKG data strip and having a size that the stylus bridges several of the perforations to minimize any tendency of the perforations to interfere with the movement of the stylus across the width of the data strip during recording;

FIG. 5 is a view like FIG. 4 but showing an EKG recording data strip constructed in accordance with another embodiment of the invention in which the perforations are formed in the back, lower surface of the strip and do not extend completely through the thickness of the strip to prevent any interference with the movement of the stylus across the width of the strip during the recording of the tracing;

FIG. 6 is a fragmentary top plan view of a record card having precoated adhesive areas for mounting individual segments and other precoated adhesive areas for mounting a number of contiguous segments forming a rhythm strip. This figure illustrates how the perforations determining the length and width of the individual segments are matched to the dimensions and areas of the precoated adhesive locations on the card;

FIG. 7 is a fragmentary top plan view like FIG. 6 but showing a different form of record card in which the tracings are retained within slide-in mounts. This FIG. 7 illustrates how the dimensions of the detachable segments of the perforated EKG data strip of the present invention are readily matched to the mounting areas of this type of record card;

FIG. 8 is a top plan view of a third form of record card (a small personal record card designed for an individual to carry with him at all times). FIG. 8 illustrates how the present invention permits the dimensions of the detached, recorded segments to be matched to the requirements of this type of record card; and FIG. 9 is a fragmentary top view like FIG. 2 but showing an EKG data strip constructed in accordance with another embodiment of the present invention and having longitudinally and laterally aligned detachable segments for receiving recordings from the plurality of styli (in this case three styli) for simultaneous tracings on a single EKG data strip.

DESCRIPTION OF THE PREFERRED EMBODIMENTS

Figure 1:
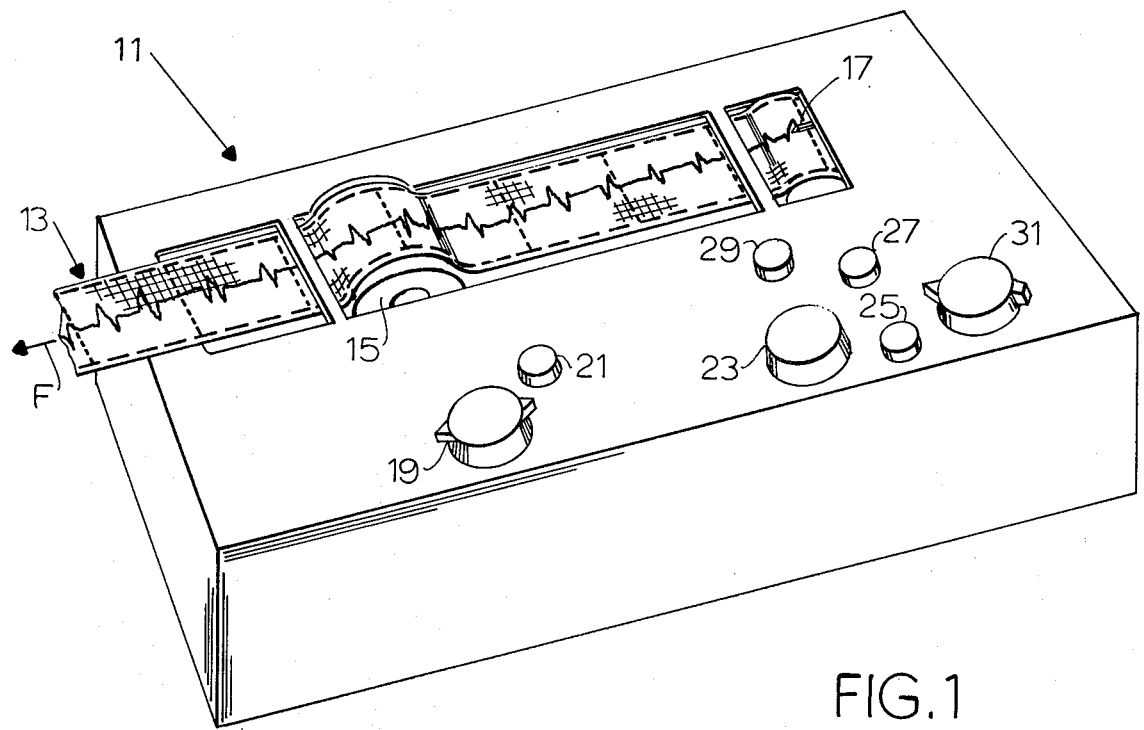
FIG. 1 is an isometric view of an electrocardiogram machine.

FIG. 1 is an isometric view of an electrocardiograph machine, indicated generally by the reference numeral 11, in the process of making heart lead tracings on an EKG data strip, indicated generally by the reference numeral 13, constructed in accordance with one embodiment of the present invention.

The EKG machine 11 includes a rubberized roller 15 which frictionally engages the underside of the data strip 13 to pull the strip forward at a precise speed in the direction shown by the arrow F.

The data strip 13 is thereby moved longitudinally beneath a stylus 17. The stylus 17 is a heated stylus and is movable across the width of the data strip 13 (upwardly and downwardly as viewed in FIG. 1) to form the tracing on the data strip by the engagement of the underside 17A (See FIG. 4) of the stylus 17 with the upper surface of the specialized EKG data strip.

The EKG machine 11 has conventional controls. These include an on-off switch 19, a speed adjustment knob 21 (which in the ordinary machine can adjust the speed from 25 to 50mm per second), a dial 23 for positioning and centering the wave form, a button 25 for registering the amplitude, a button 27 for marking the data strip with the type of lead being recorded, a sensitivity adjustment dial 29 (which in a particular machine can adjust the sensitivity by factors of 2, 1, ½, and ¼), and a lead selector dial or switch 31 for selecting a particular lead to be recorded.

Figure 2:
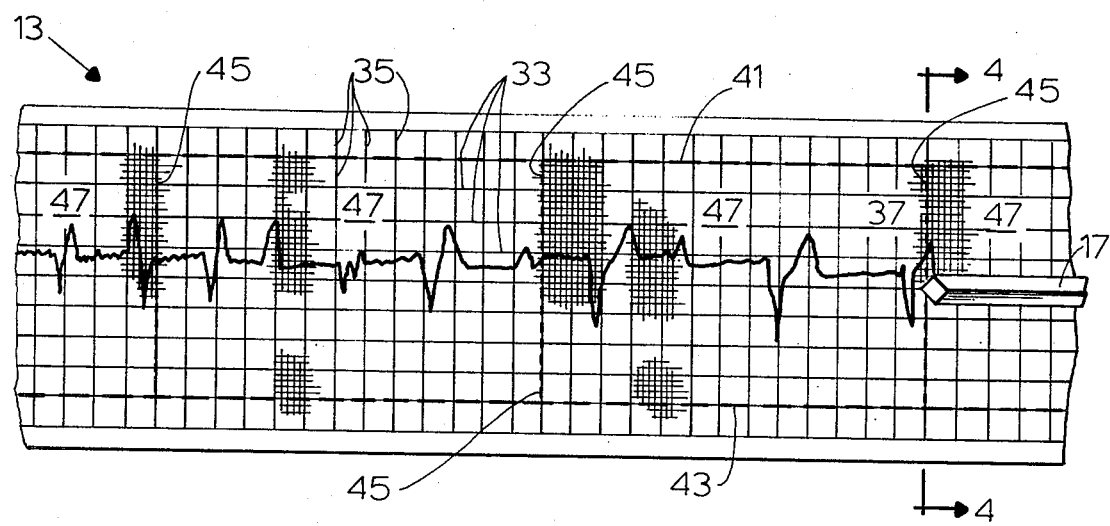
FIG. 2 is a top plan view showing a heart lead tracing as recorded on an EKG data strip constructed in accordance with one embodiment of the present invention.

As best illustrated in FIG. 2, the EKG data strip 13 has a central part which is marked off with parallel longitudinally extending grid lines 33 and transversely extending grid lines 35 to form a chart. The chart provides a background for the tracing 37 formed on the data strip by the stylus 17.

After a particular heart lead tracing has been recorded on the data strip 13, it is usually necessary to transfer that tracing, or at least a typical part of it, to a permanent record file for that patient. Prior to the present invention this had been a laborious and time consuming process. Since the doctor usually did not cut out the particular part of the data strip required, the doctor in most cases had to mark the part of the data strip required with an indication of the lead involved. A technician then had to cut out and mount the parts of the data strip so marked.

With the prior art devices, it was necessary either to manually cut the parts out by scissors or to use some sort of cutting machine (which had the drawback of inefficiency and inflexibility as pointed out in detail in the introduction above).

The present invention provides a method and a system which really simplifies the recording, detachment and transfer of the recordings to a permanent record file.

In accordance with the present invention, a single channel recording strip as illustrated in FIG. 2 has a first longitudinally extending line of perforations 41 formed adjacent one side edge of the EKG data strip 13 and a second longitudinal line of perforations 43 formed adjacent to the other side edge of the strip.

A plurality of transverse lines of perforations 45 are formed across the EKG data strip 13 to extend between the first and second longitudinal lines of perforations 41 and 43. The transverse lines of perforations 45 are located at spaced intervals along the length of the EKG strip to thereby dividing the central part of the strip into a plurality of longitudinally aligned segments 47, each of which has a predetermined width between the longitudinal perforations and a predetermined length between two adjacent transverse perforations, and each of which is readily detachable from the EKG data strip along the longitudinal and transverse perforations. The segments 47 can be detached as separate, individual segments, or a number of segments can be detached as a unit (as is required to provide a rhythm strip).

FIGS. 3A through 3D show how an individual segment 47 is detached from the rest of the EKG data strip 13 and transferred to a record card. FIGS. 3B and 3C show the detached segment 47 being transferred (as indicated by the arrows T) to a space 49 on a permanent record card 51 (see FIGS. 3C and 3D).

The record card 51 shown in FIG. 3D has a number of mounting locations 49 adapted to receive different segments 47 representing different heart leads.

As best illustrated in FIG. 6, the card 51 has spaces 49 which are coated with an adhesive so that the recording segment 47 need only be pressed into place. As also illustrated in FIG. 6, the card 51 has one or more spaces for receiving a rhythm strip 53 made up of a row of connected segments 47 as illustrated.

It is an important feature of the present invention that the segments 47 can be readily dimensioned to provide an exact fit for the recordings to be stored on a particular record card.

FIGS. 7 and 8 illustrate this fact with added detail.

In FIG. 7, the record card 51 includes slide-in mounts which retain the recordings behind side and end retaining edges 55 and 57 (as shown partly broken away in the top left hand corner of FIG. 7).

FIG. 8 shows a relatively small, personal record card adapted to be carried by the patient on his person for ready reference in the event of an emergency. In this case the individual segments are relatively small and each tracing 37 can also be made at a relatively low gain so that the entire record can be kept small. With this particular file record form the adhesive locations 49 are sometimes made circular as shown in FIG. 8.

As illustrated in FIG. 9, the present invention is also readily adapted to the newer EKG recording machines which record a plurality of channels simultaneously on a wider than normal EKG data strip 13.

In the particular embodiment shown in FIG. 9, the EKG machine is set up to record three channels simultaneously and has three recording styli 17. As illustrated in FIG. 9, additional longitudinally lines of perforation 59, 61, 63 and 65 are formed in the central part of the data strip 13 to divide the strip into the three parallel extending strips of segments 47 as illustrated.

It is an important feature of the present invention that the perforations can be formed in the special EKG data strip in this way to easily and readily accommodate new advancements and modifications in the machine recording arrangements. In contrast the multiple channel recording strip shown in FIG. 9 is difficult (and in some cases impossible) to use with the extending cutting machine.

As illustrated in FIGS. 4 and 5, the transverse perforations 45 are preferably kept quite small in size so that the underside 17A of the stylus 17, which is a relatively wide surface, bridges across several of the perforations 45. This minimizes any tendency of the perforations 45 to interfere with normal movement of the stylus 17 across the data strip 13 when the perforations are formed completely through the data strip as illustrated in FIG. 4.

In some cases it is also preferable to form the perforations, so that the perforations 45 are cut into the lower, back side of the data strip 13 and terminate beneath the upper surface of the data strip 13. This is illustrated in FIG. 5 and is an additional safeguard against interference with the movement of the stylus 17.

The way in which the data strip 13 is perforated in accordance with the present invention has further advantages in operation. The machine operator can readily determine whether the maximum amplitude of the recording will fall within the boundaries of the outer perforations 41 and 43, and he can make an appropriate adjustment in the amplitude to bring all of the signal within this width of the data strip if such an adjustment is necessary. This is quite desirable because the prior art cutting devices have presented the problem of clipping off the upper and lower peaks of the recordings in some instances. With the present invention the operator can see exactly where the segment 47 will be detached from the rest of the strip, and he can make sure that the entire amplitude of the recording is maintained within this width.

In the present invention the operator can also visually see when the recording has passed over one of the transverse lines of perforations 45 and can shut off the machine so that the recording will be completed at or closely adjacent to the particular transverse line of perforation 45 desired. This is an important economic consideration because the specialized EKG paper is relatively expensive and there is a tendency, particularly with new technicians, to record longer than necessary tracings.

While we have illustrated and described the preferred embodiments of our invention, it is to be understood that these are capable of variations and modification and we therefore do not wish to be limited to the precise details set forth, but desire to avail ourselves such changes and alterations as fall within the purview of the following claims.

We claim:

1. A method of preparing an electrocardiogram (EKG) data strip for individual heart lead tracings to be transferred into a permanent record file, said method comprising, forming a first longitudinal line of perforations adjacent one side edge of an EKG data strip, forming a second longitudinal line of perforations adjacent to the other side edge of the EKG data strip, and forming a plurality of transverse lines of perforations across the EKG data strip between said first and second longitudinal lines of perforations and at spaced intervals along the length of the EKG strip to thereby divide the central part of the strip into a plurality of longitudinally aligned segments, each of which has a predetermined width between the longitudinal perforations and a predetermined length between two adjacent transverse perforations and each of which is readily detachable from the EKG data strip along the longitudinal and transverse perforations and including recording a heart tracing on the EKG data strip between the first and second longitudinal lines and detaching the part of the data strip bearing the recorded tracing from the rest of the strip by tearing along the longitudinal and transverse line bounding the recording, said step of recording the heart tracing including recording the tracing with a stylus mounted for movement in a direction across the width of a segment on the upper surface of the data strip with changes in amplitude of the heart trace signal, moving the data strip longitudinally beneath the stylus by a friction drive roller which frictionally engages the underside of the data strip and wherein the EKG data strip upper surface is formed with a line grid and the transverse perforations have individual serrations sufficiently smaller than the width of the stylus engaged with the data strip that the stylus bridges the perforations to prevent the perforations from interfering with the movement of the stylus with respect to the data strip during recording.

2. The invention defined in claim 1 where the detached part comprises a single segment bounded by the first and second longitudinal lines and two immediately adjacent transverse lines of perforation.

3. The invention defined in claim 1 wherein the detached recording comprises a rhythm strip comprising a plurality of adjacent segments connected together by an undetached transverse perforation line between the adjacent segments.

4. The invention defined in claim 1 including calibrating and regulating the amplitude of the heart trace signal, in the course of recording the heart tracing, against the existing width between the first and second longitudinal lines of perforation to insure that the full amplitude of the tracing is recorded within the width of the detachable segment.

5. The invention defined in claim 1 including starting the tracing adjacent one transverse line of perforation, watching for a second, selected transverse perforation to pass beneath the stylus, and discontinuing the recording adjacent to and prior to the second, selected transverse line of perforation to thereby utilize only a single segment of the length of the EKG data strip for that particular tracing.

6. The method defined in claim 1 wherein the width and length of said segments are dimensioned to fit certain spaces in a permanent record file and including transferring the detached part of the EKG data strip to a location in a permanent record file dimensioned to receive and permanently display said detached part.

7. The invention defined in claim 6 including adhering the detached part to a precoated adhesive location in the permanent record file.

8. The invention defined in claim 6 including slipping the detached part into a frame in the permanent record file.

9. The invention defined in claim 1 wherein the perforations are formed on the lower, back face of the strip so as not to extend into the upper grid surface to prevent any interference with the movement of the stylus across the width of the strip during the recording of the tracing.

10. The invention defined in claim 1 including forming additional longitudinal lines of perforations between the first and second lines of perforations to subdivide the width of the data strip into separate channels for receiving simultaneous tracings from multiple styli.

11. An electrocardiogram (EKG) data strip of the kind used for individual heart lead tracings which are transferred into a permanent record file, said data strip comprising, an elongated strip having an EKG chart on an upper surface for engagement by a movable stylus of an EKG recording machine during the recording of an individual heart lead tracing on the upper surface of the strip, a first longitudinal line of perforations formed adjacent one side edge of the data strip, a second longitudinal line of perforations formed adjacent the other side edge of the data strip, and a plurality of transverse lines of perforations formed across the data strip between the first and second longitudinal lines of perforations and at spaced intervals along the length of the EKG strip to thereby divide the central part of the strip into a plurality of longitudinally aligned segments, each of which has a predetermined width between the longitudinal perforations and a predetermined length between two adjacent transverse perforations and each of which is readily detachable from the EKG data strip along the longitudinal and transverse perforations and wherein the transverse perforations have individual serrations sufficiently smaller than the width of the stylus engageable with the data strip that the stylus bridges the perforations to prevent the perforations from interferring with the movement of the stylus with respect to the data strip during recording.

12. The invention defined in claim 11 wherein the data strip is a heat sensitive strip for recording a tracing in response to engagement by a heated stylus.

13. The invention defined in claim 11 including an additional longitudinal line of perforations disposed parallel to and between the first and second longitudinal lines of perforations for dividing the data strip into a plurality of parallel extending channels for recording a plurality of tracings simultaneously.

14. A system of the kind in which individual heart lead tracings are recorded on an electrocardiogram (EKG) data strip and then detached from the strip and transferred to a permanent file record, said system comprising, an EKG data strip having a first longitudinal line of perforations formed adjacent one side edge of the data strip, a second longitudinal line of perforations formed adjacent to the other side edge of the data strip, a plurality of transverse lines of perforations each formed of individual serrations and extending across the EKG data strip between said first and second longitudinal lines of perforations and at spaced intervals along the length of the EKG strip to thereby divide the central part of the strip into a plurality of longitudinally aligned segments, each of which has a predetermined width between the longitudinal perforations and a predetermined length between two adjacent transverse perforations and each of which is readily detachable from the the EKG data strip along the longitudinal and transverse perforations, an EKG recording machine for recording the individual heart lead tracings on said segments and within the width of said segments in the central portion of the EKG data strip between the first and second longitudinal lines of perforations, said EKG recording machine including a stylus mounted for movement in a direction across width of a segment on the upper surface of the data strip, said stylus having a width in the area in contact with the data strip sufficiently greater than the size of the individual serrations in the transverse perforations that the stylus bridges the transverse perforations to prevent the perforations from interfering with the movement of the stylus with respect to the data strip during recording, said EKG recording machine also including a friction drive roller engageable with the lower surface of the data strip to frictionally drive the data strip longitudinally beneath the stylus during recording of a heart tracing, and a file record having storage spaces matched to the dimensions of said segments for retaining the segments in place on the record file after they have been detached from the EKG data strip and transferred to the record file.

15. The invention defined in claim 14 wherein the file record includes storage spaces having a length dimensions which are multiples of the length of an individual segment of the EKG data strip.

16. The invention defined in claim 14 wherein the storage spaces contained precoated adhesive for retaining the segments in place.

17. The invention defined in claim 14 wherein the longitudinal perforations have a length greater than the length of the transverse perforations.

* * * * *